United States Patent [19]

Chan et al.

[11] Patent Number: 4,633,015

[45] Date of Patent: Dec. 30, 1986

[54] PRODUCTION OF ADIPIC ACID FROM 1,4-DISUBSTITUTED-2-BUTENE

[75] Inventors: Albert S. C. Chan, St. Charles; Donald E. Morris, Kirkwood, both of Mo.

[73] Assignee: Monsanto Company, St. Louis, Mo.

[21] Appl. No.: 669,910

[22] Filed: Nov. 9, 1984

[51] Int. Cl.$^4$ .................. C07C 27/02; C07C 51/09; C07C 55/14
[52] U.S. Cl. .................. 562/590; 560/204; 560/190
[58] Field of Search .................. 562/590; 560/204, 190

[56] References Cited

U.S. PATENT DOCUMENTS

| | | | |
|---|---|---|---|
| 4,189,599 | 2/1980 | Kesling et al. | 560/204 |
| 4,259,519 | 3/1981 | Stille | 560/204 |

*Primary Examiner*—Werren B. Lone
*Attorney, Agent, or Firm*—Thomas N. Wallin

[57] ABSTRACT

The dicarbonylation product of 1,4-disubstituted-2-butene is useful as intermediate in the production of adipic acid, hexamethylenediamine and 1,6-hexanediol. It is produced by carbonylating a solution of the disubstituted butene in a polar, aprotic non-basic solvent at 80°–140° C. in the presence of a catalyst comprised of a halide of the transition metal. The dicarbonylation product is converted to adipic acid by hydrogenation followed by hydrolysis.

19 Claims, No Drawings

PRODUCTION OF ADIPIC ACID FROM 1,4-DISUBSTITUTED-2-BUTENE

BACKGROUND OF THE INVENTION

A. Field of the Invention

The invention relates to the production of adipic acid from 1,4-disubstituted-2-butenes.

Adipic acid is produced at a worldwide capacity of nearly five billion pounds, most of which is used as a raw material for nylon 66 polymer production. It is produced commercially by the air oxidation of cyclohexane to a cyclohexanone/cyclohexanol mixture (KA oil) which is subsequently oxidized to adipic acid with nitric acid. Adipic acid is also produced commercially from phenol by hydrogenation to cyclohexanol, the cyclohexanol being subsequently oxidized with nitric acid to adipic acid. Although adipic acid has been so produced for nearly forty (40) years, there are two major disadvantages in the current commercial processes. The air oxidation of cyclohexane must be carried out at low conversion rates in order to achieve high selectivity; and the recycling of large amounts of cyclohexane is potentially hazardous. Benzene which is the hydrocarbon source, is not expected to continue to be a low cost material.

U.S. Pat. No. 4,166,913 to ARCO describes production of adipic acid from carbon monoxide and butadiene. The ARCO process can be summarized by the following equations:

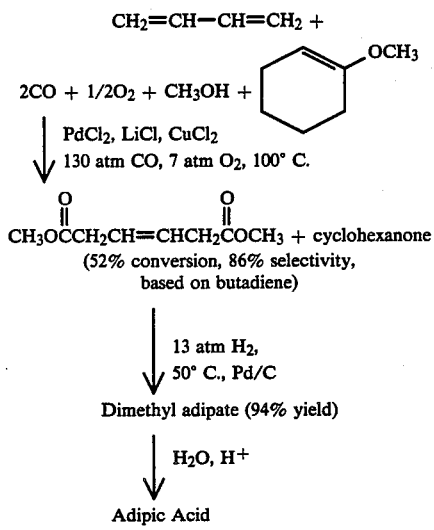

The need for dehydrating agents and the potential safety hazard of the high pressure $CO/O_2$ mixture under catalytic reaction conditions are significant disadvantages in the practice of the above production method.

A second known alternative to the production of adipic acid is described in U.S. Pat. Nos. 4,169,956 and 4,171,451 to BASF. The process can be summarized schematically as follows:

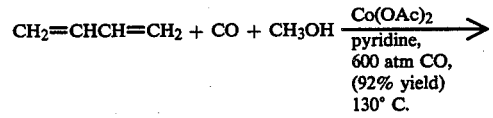

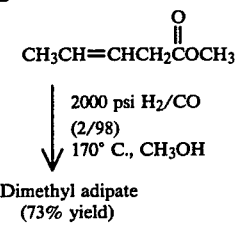

A major disadvantage in this process is the extremely high reaction pressure required in the carbonylation step.

Previous attempts to dicarbonylate 1,4-disubstituted-2-butenes have been relatively unsuccessful. In the attempt described by Medema, D.; van Helden, R.,; Kohll, C. F. *Inorg. Chim. Acta.*, 3 (1969) 155, page 20, it was reported that only 3% of 3-pentenoyl chloride was obtained in the attempt to dicarbonylate 1,4-dichloro-2-butene. No dicarbonylated product was observed. In the dicarbonylation attempt described by Imamura, S.; Tsuji, J.; *Tetrahedron* 25 (1969) 4187, it was observed that only about 10–37% of linear dicarbonylated products were obtained in a palladium chloride-catalyzed carbonylation of 1,4-diethoxy-2-butene; and that large amounts of by-products resulted from isomerization and hydrogenolysis of the starting material or reaction intermediates.

If a method for the production of adipic acid could be found based on the less expensive butenes, or derivatives thereof, without the problems of hydrogenolysis and isomerization described above, such a method would be a significant advance in the art and is an object of this invention.

SUMMARY OF THE INVENTION

According to this invention, adipic acid is produced by carbonylating a solution of the 1,4-disubstituted-2-butene in an aprotic, polar, non-basic solvent, in the presence of a catalyst comprised of a halide of a transition metal. The dialkyl hex-3-enedioates produced are converted to dialkyl adipate by hydrogenation, and subsequently to adipic acid by hydrolysis essentially as described in U.S. Pat. No. 4,189,599, hereby incorporated by reference.

DETAILED DESCRIPTION OF THE INVENTION

The catalytic dicarbonylation of 1,4-disubstituted-2-butene is shown in reaction form as follows:

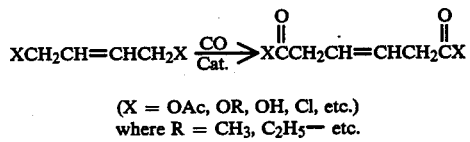

(X = OAc, OR, OH, Cl, etc.)
where R = CH$_3$, C$_2$H$_5$— etc.

The catalyst may be any transition metal halide, but palladium chloride is preferred. Other palladium halides such as palladium bromide and, to a lesser extent, palladium iodide have been found to be effective but to a much lower yield than the palladium chloride. Other transition metal salts such as nickel chloride have also been found to be effective but to a much lower yield than palladium chloride.

As indicated above, the dialkyl hex-3-enedioates are produced by carbonylating a solution of 1,4-disubstituted-2-butene in an aprotic, polar non-basic solvent, in the presence of a catalyst comprising a halide of a transition metal.

Polar, aprotic non-basic solvents are required for high catalyst activity and high selectivity to the desired linear dicarbonylated products. Solvents of high polarity are required in order to maintain the solubility of the metal catalyst and thus high catalyst activity; aprotic solvents are necessary in order to obtain high selectivity to the linear dicarbonylated product. The presence of protic solvents causes isomerization and hydrogenolysis products. The presence of solvents which are too basic results in poorly active or inactive catalysts. Suitable solvents are known to include nitriles such as benzonitrile, propionitrile, isobutyronitrile, acetonitrile, and trimethylacetonitrile. Dipolar, aprotic, non-basic solvents of similar donor properties to those of the nitriles, such as bis(2-methoxyethyl)ether (diglyme), methylene chloride, and 1,4-dimethoxy-2-butene will also serve suitably as a solvent in the reaction. Other solvents expected to fall in this category include nitrobenzene, nitromethane, ketones and the like. When aprotic, relatively poor alpha-donor solvents such as carbon tetrachloride, toluene, and benzene were employed, very little reaction was observed. For example, only 55% substrate conversion was obtained when the reaction was attempted in toluene. This may be compared to the 90 to 100% substrate conversions obtained when the reaction is run in the preferred solvents mentioned above. When polar, aprotic, but more basic solvents such as N,N-disubstituted-amides were employed, again low conversions are obtained. For example, only 8% substrate conversion was obtained when the reaction was attempted in N,N-dimethylformamide. When polar, non-basic, but protic solvents such as alcohols are employed low selectivities to the desired linear dicarbonylated products are obtained (see Example 4). A comparison of solvent systems is shown in Table 1, where the carbonylation reaction was conducted as in Example 1 except as otherwise noted.

peratures. A reaction temperature of about 80°–140° C. has been found to be suitable for the compromise of rates and selectivity. Lewis acids have been found to significantly increase the rates of reaction, but at some sacrifice of selectivity.

The hydrogenation of the dialkyl hex-3-enedioates to dimethyl adipate followed by hydrolysis to adipic acid is essentially as described in U.S. Pat. No. 4,189,599, hereby incorporated by reference, or by state-of-the-art improvements thereto.

EXAMPLES SHOWING DICARBONYLATION ONLY

Example 1

A 300 ml Hastelloy B autoclave equipped with a Magnedrive stirrer was charged with 0.44 g $PdCl_2$ (2.5 mmol), 2.6 g 1,4-dimethoxy-2-butenes (over 90% trans, 22.4 mmol) and 70 g isobutyronitrile solvent. The solution was heated under 2500 psig CO to 100° C. The reaction was allowed to proceed for 20 hours at 100° C. under 199 atm CO. G.C. analyses of the final solution indicated over 99% converrsion of 1,4-dimethoxy-2-butenes. 72% yield of dimethyl-3-hexenedioate

and 15% yield of

were obtained.

Example 2

Same as example 1 except that the materials charged were 0.44 g $PdCl_2$ (2.5 mmol), 2.5 g CuCl (25 mmol), 7.5 g 1,4-dimethoxy-2-butenes (over 90% trans, 65 mmol), and 67.5 g acetonitrile solvent. G.C. analyses of the final product after 21 hours of reaction indicated over 99%

TABLE 1

Comparison of Solvent Systems for the $PdCl_2$—Catalyzed Carbonylation of 1,4-Dimethoxy-2-butene

| Solvent | Reaction Time (hours) | % Conversion | % Yield of $CH_3CH=CHCH_2CO_2CH_3$ (cis + trans) | % Yield of $CH_3OCHCH_2CH=CHCH_2CO_2CH_3$ (cis + trans) | % Yield of $CH_3O_2CCH_2CH=CHCH_2CO_2CH_3$ (cis + trans) |
|---|---|---|---|---|---|
| $C_6H_5CN$ | 24 | 100 | 3 | 3 | 78 |
| $CH_3CN$ | 20 | 94 | 3 | 41 | 33 |
| $(CH_3)_2CHCN$ | 20 | 92 | 4 | 48 | 33 |
| Diglyme | 22.5 | 91 | 6 | 55 | 35 |
| $CH_2Cl_2$ | 22 | 100 | 2 | 4 | 74 |
| Toluene | 23.5 | 55 | 2 | 31 | 2 |
| DMF | 24 | 8 | — | 1 | 0 |
| HMPA | 24 | | Virtually no reaction | | |
| $DM_2$—$B^b$ | 48 | 91 | <1 | 57 | 25 |

$^a$[$Pdcl_2$] = 2.5 × $10^{-2}$ M; [$CH_3OCH_2CHCHCH_2OCH_3$] = 1 M; Pco = 199 atm; T = 100° C.
DMF = nin-dimethylformamide; HMPA = hexamethylphosphoramide; DM-2—B = 1,4-dimethoxy-2-butene.
$^b$The substrate is also solvent. [$CH_3OCH_2CHCHCH_2OCH_3$] = 7.9 M.

In order to optimize the rates and selectivity for the dicarbonylation of 1,4-disubstituted-2-butene, the temperature dependence of this reaction has been studied. As expected, the reaction rates increase with the increase of reaction temperature. However the starting material begins to decompose and polymerize at higher temperatures. Catalyst deactivation via precipitation of palladium metal is also more severe at the higher temconversion of 1,4-dimethoxy-2-butenes. 71% yield of dimethyl-3-hexenedioate

9% yield of

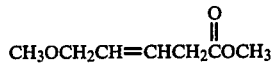

and 7% yield of

were observed.

Example 3

Same as 1 except that the materials charge were 0.44 g PdCl$_2$ (2.5 mmol), 12.2 g 1,4-dimethoxy-2-butene (over 90% cis, 105 mmol), and 86.3 g benzonitrile (solvent). G.C. analyses of the products after 24 hours indicated over 99% conversion of 1,4-dimethoxy-2-butene. 78% yield of

3% yield of

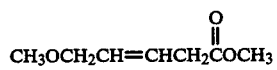

and 3% yield of

were observed.

What is claimed is:

1. A process for the production of adipic acid from 1,4-dialkoxy-2-butene comprising carbonylating a solution of 1,4-dialkoxy-2-butene in an aprotic polar non-basic solvent selected from the group consisting of nitriles, 1,4-dimethoxy-2-butene, methylene chloride and bis(2-methoxyethyl)ether at 80°–140° C. in the presence of a catalyst selected from the group consisting of palladium halides and nickel halides thereby forming dialkyl hex-3-enedioate and hydrogenating the said dialkyl hex-3-enedioate to form alkyl adipate, and subsequently hydrolyzing the dialkyl adipate to adipic acid.

2. The process of claim 1 wherein the 1,4-dialkoxy-2-butene is 1,4-dimethoxy-2-butene.

3. The process of claim 1 wherein the solvent is a nitrile.

4. The process of claim 1 wherein the solvent is proprionitrile.

5. The process of claim 1 wherein the solvent is isobutyronitrile.

6. The process of claim 1 wherein the solvent is acetonitrile.

7. The process of claim 1 wherein the solvent is trimethylacetonitrile.

8. The process of claim 1 wherein the solvent is bis(2-methoxyethyl)ether.

9. The process of claim 1 wherein the solvent is benzonitrile.

10. The process of claim 1 wherein the solvent is methylene chloride.

11. The process of claim 1 wherein the catalyst is a palladium dihalide.

12. The process of claim 11 wherein the catalyst is palladium diiodide.

13. The process of claim 11 wherein the catalyst is palladium dibromide.

14. The process of claim 11 wherein the catalyst is palladium dichloride.

15. The process of claim 1 wherein the catalyst is nickel chloride.

16. The process of claim 1 wherein the catalyst is formed in situ.

17. A process for the production of adipic acid from 1,4-diacetoxy-2-butene comprising carbonylating a solution of 1,4-diacetoxy-2-butene in an aprotic polar, non-basic solvent selected from the group consisting of nitriles, 1,4-dimethoxy-2-butene, methylene chloride and bis(2-methoxyethyl)ether at 80° to 140° C. in the presence of a catalyst selected from the group consisting of palladium halides and nickel halides thereby forming dialkyl hex-3-enedioate; hydrogenating the said dialkyl hex-3-enedioate to dialkyl adipate; and hydrolyzing the dialkyl adipate to adipic acid.

18. A process for the production of adipic acid from 1,4 dichloro-2-butene comprising carbonylating a solution of 1,4-dichloro-2-butene in an aprotic, polar non-basic solvent selected from the group consisting of nitriles, 1,4-dimethoxy-2-butene, methylene chloride and bis(2-methoxyethyl)ether at 80° to 140° C. in the presence of a catalyst selected from the group consisting of palladium halides and nickel halides thereby forming dialkyl hex-3-enedioate; hydrogenating the said dialkyl hex-3-enedioate to dialkyl adipate; and hydrolyzing the dialkyl adipate to adipic acid.

19. A process for the production of adipic acid from 2-butene-1,4-diol comprising carbonylating a solution of 2-butene-1,4-diol in an aprotic, polar, non-basic solvent selected from the group consisting of nitriles, 1,4-dimethoxy-2-butene, methylene chloride and bis(2-methoxyethyl)ether at 80° to 140° C. in the presence of a catalyst selected from the group consisting of palladium halides and nickel halides thereby forming dialkyl hex-3-enedioate; hydrogenating the said diaklyl hex-3-enedioate to dialkyl adipate; and hydrolzing the dialkyl adipate to adipic acid.

* * * * *